United States Patent [19]
Andre et al.

[11] 3,993,596
[45] Nov. 23, 1976

[54] PREPARATION OF SPHEROIDAL ALUMINA PARTICLES

[75] Inventors: Jacques Maurice Jules Ghislain André; Raymond Marc Cahen, both of Brussels; Henri Robert Debus, Meise; René Odon Lammers, Brussels; Hugo Johannes Van Thillo, Grimbergen, all of Belgium

[73] Assignee: Labofina S.A., Brussels, Belgium

[22] Filed: Feb. 10, 1975

[21] Appl. No.: 548,192

[30] Foreign Application Priority Data
Feb. 18, 1974 Luxembourg............................ 69406

[52] U.S. Cl.................................. 252/448; 252/430; 252/439; 252/441; 252/463; 252/465; 252/466 J; 252/466 PT
[51] Int. Cl.$^2$.......................................... B01J 37/00
[58] Field of Search......... 252/448, 430, 465, 466 J, 252/466 PT, 439, 463, 441

[56] References Cited
UNITED STATES PATENTS

| | | | |
|---|---|---|---|
| 2,492,167 | 12/1949 | Marisic et al. | 252/448 |
| 2,819,230 | 1/1958 | Strecker | 252/465 |
| 3,120,495 | 2/1964 | Innes | 252/448 |
| 3,558,508 | 1/1971 | Keith | 252/448 X |

*Primary Examiner*—Patrick P. Garvin

[57] ABSTRACT

A process for preparing catalysts in the form of beads comprising at least a catalytic agent and an alumina carrier, said process comprising polymerizing in a hot and substantially water-immiscible fluid, an aqueous mixture which comprises alumina hydrogel, alumina hydrosol and a compound capable of generating a catalytic agent and a water soluble monomer whose un-cross-linked polymer is water soluble or forms a gel, such aqueous mixture being dispersed as droplets into the hot fluid, recovering beads from said water-immiscible fluid and drying and calcining said beads.

9 Claims, No Drawings

3,993,596

PREPARATION OF SPHEROIDAL ALUMINA PARTICLES

BACKGROUND OF THE INVENTION

The present invention relates to a process for preparing catalysts. More particularly, the present invention relates to a process for preparing catalysts in the form of beads, said beads comprising a catalytic agent and an alumina carrier. The present invention also relates to the catalysts so obtained.

Alumina is widely used as constituent of industrial catalysts for converting hydrocarbons and various organic compounds. For most of such applications, catalysts in the form of spheroidal particles or beads preferably are used. Among the main advantages of such beads are better wear and crushing strength and a more regular distribution in the reactors which reduces the pressure drop of the reactants passing through the reactors. Generally, the bead type catalysts comprising a catalytic agent and an alumina carrier, are prepared by impregnating alumina beads with a catalytic agent or with a compound which generates this catalytic agent by thermal or chemical treatment.

Several processes have already been proposed for preparing spheroidal alumina particles. One such process consists of dispersing an alumina hydrosol as droplets into a medium wherein gelation occurs, and thereafter, subjecting the beads which are obtained in the form of alumina hydrogel, to one or more aging treatments in order to obtain beads having a suitable mechanical resistance. According to another process, an alumina hydrosol is mixed with an ammonium salt and a synthetic polymer or a natural gum. The mixture is then dispersed into a water-immiscible medium and thereafter subjected to an aging treatment. Alumina beads prepared by some of these processes contain high amounts, even excessive sometimes, of impurities which are undesirable when these beads are used as catalysts or catalyst supports.

An object of the present invention is to provide a new and simple method for preparing catalysts in the form of spheroidal particles, consisting of one or more calalytic agents and an alumina carrier.

Another object of the present invention is to provide a new process for preparing catalyst particles whose catalytic activity is not inhibited by impurities.

A further object of the present invention is to provide a process to obtain catalyst beads having an improved mechanical strength.

Additional objects will become apparent from the following description of the invention herein disclosed.

SUMMARY OF THE INVENTION

The present invention is a process for preparing spheroidal catalysts particles on an alumina support, such process comprising polymerizing in a hot and practically water-immiscible fluid, an aqueous mixture which comprises alumina hydrogel and hydrosol, a compound which generates active catalytic agent and a water-soluble monomer whose uncross-linked polymer is water-soluble or forms a gel, this mixture being dispersed as droplets into the polymerization zone. More particularly, the process of the invention comprises (a) producing an aqueous mixture which comprises alumina hydrogel and hydrosol, a compound which generates an active catalytic agent, and a monomer as hereinabove defined, the aqueous mixture being easily dispersed as droplets into a hot and practically water-immiscible fluid, (b) polymerizing the monomer contained in each droplet of said aqueous mixture, (c) recovering beads therefrom consisting of alumina hydrogel and hydrosol and of a compound which generates an active catalytic agent, all agglomerated by the polymer, and (d) drying and calcining said beads, said beads consisting essentially of alumina and said catalytic agent.

Another embodiment of the process of the invention comprises preparing an aqueous mixture comprising from 5 to 29.95% by weight (based on aluminium oxide) of alumina hydrogel and hydrosol, 0.05 to 10% by weight of a compound which generates an active catalytic agent (based on catalytic constituent), the total amount of hydrogel, hydrosol and catalytic agent not exceeding 30% by weight, 0.25 to 20% by weight of a water-soluble monomer, ethylenically unsaturated, whose uncross-linked polymer is water-soluble or forms a gel, and 0.05 to 2% by weight of a polymerization catalyst, dispersing said aqueous mixture, as droplets, in a water-immiscible fluid maintained at a temperature of 50° to 105° C, at atmospheric pressure, maintaining the droplets in this fluid until beads are formed and become hard, and drying or drying and calcining said beads.

DESCRIPTION OF THE PREFERRED EMBODIMENTS

In the use of the process of the present invention, alumina hydrogel is used in a finely divided form in order to ensure an easy dispersion into the starting aqueous mixture. Alumina hydrogel may be prepared by any known method, preferably by treating aluminium sulphate with a base, by hydrolyzing aluminium isopropylate or by treating an alkali aluminate with an acid or with aluminium sulphate. The precipitate obtained is waterwashed and dried. The exact composition of alumina hydrosols is not fixed. The hydrosols may be prepared from aluminium bromide, aluminium sulphate, aluminium alcoholate, or preferably from aluminium chloride, or by digesting metallic aluminium in hydrochloric acid or in hydrated aluminium chloride. In the latter case, it may be considered that the hydrosols have the following formula:

$$x \, (Al(OH)_3 - Al\,Cl_3)$$

wherein $x$ is an integer between 4 and 6. The terms "alumina hydrogel" and "alumina hydrosol" include not only these compounds in pure state but also, these compounds containing a low amount of silica or silicate or similar material.

The starting aqueous mixture must remain sufficiently free flowing at room termperature to allow an easy dispersion thereof in the form of droplets into the polymerization mixture. In order to avoid excessive investment and drying costs of the beads obtained by the process, too dilute solutions of the starting aqueous mixture are to be avoided. Preferably, the aqueous mixtures which are used contain in a finely divided form, from 5% to 30% by weight of alumina hydrogel and hydrosol (based on dry aluminium oxide). In some cases, when an acid monomer is used, the aqueous mixture of alumina hydrogel an hydrosol becomes thixotropic or may be thickened with the formation of an irreversible gel. This stiffening (which does not result from a polymerization of the monomer) may be avoided by subjecting the aqueous mixture to a vigorous stirring. Advantageously, starting mixtures may be used containing no more than 10 to 20% by weight of alumina hydrogel and hydrosol (based on aluminium oxide). When basic monomers are used, the alumina hydrogel and hydrosol content in the starting aqueous mixture may be higher, but without exceeding about 30% by weight (based on $Al_2O_3$).

In the starting aqueous mixture, the weight ration of alumina hydrogel to alumina hydrosol may vary between wide limits, generally, however, between 99 : 1 and 50 : 50 and more particularly, between 85 : 15 and 55 : 45, the weights of hydrogel and hydrosol being based on $Al_2O_3$. A preferred embodiment for preparing the starting aqueous mixture comprises digesting hydrogel into hydrosol, this treatment being accelerated by increasing temperature. The hydrogel plus hydrosol content may vary in the starting aqueous mixture, and also the hydrogel to hydrosol ratio, to the extent the aqueous mixture remains sufficiently free flowing to be easily dispersed in finely divided droplets into the polymerization mixture. Those skilled in the art may readily determine the optimum conditions for obtaining such fluid mixture in view of the teachings herein.

Each catalyst generating compound introduced into the starting aqueous mixture may be either this agent itself, particularly a metallic oxide, sulfide, or metal, or a compound which gives such active agent by thermal or chemical treatment. In other words, for preparing a catalyst which consists of alumina and cobalt oxide, either cobalt oxide, or a cobalt salt such as cobalt chloride, acetate, carbonate or nitrate may be used. When it is desired to obtain a catalyst containing alumina and catalytic metal, a compound of this metal generally is used. By way of example, rhenium chloride, chloroplatinic acid, platinium-tetramine chloride, $Pt(NH_3)_4 Cl_2$, ammonium palladium-chloride, $(NH_4)_2 Pd Cl_4$ and similar compounds used as a precursor for the metal contained therein, for catalytic metal deposition. In order to obtain a catalyst in which the active agent is highly dispersed, a catalyst generating compound which is water-soluble or which forms a gel or which forms a colloidal suspension preferably is used. A catalyst consisting of alumina and catalytic metal also may be manufactured by preparing, according to the process of the present invention, alumina which contains metal oxide in a finely divided form and thereafter subjecting such to hydrogenation conditions according to known methods.

The amount of the compound which generates the active catalytic agent introduced into the starting aqueous mixture generally is between 0.05 and 35% or higher of the weight of the aqueous mixture. The exact amount depends on many factors such as catalyst type desired, particular catalyst generating compound used, etc. The amount most often, however, will vary between about 0.05 and 10% by weight, such amount being based on active catalytic agent in the final catalyst. For starting aqueous mixture to remain sufficiently free flowing at room terrmperature, the total amount of alumina hydrogel and hydrosol (based on $Al_2O_3$) and of catalytic agent generating compounds (based on active catalytic agents) usually does not exceed about 30% of the weight of the aqueous mixture.

The water-soluble monomer whose uncross-linked polymer is water-soluble or forms a gel is selected from the group consisting of ethylenically unsaturated compounds comprising acrylic compounds of general formula

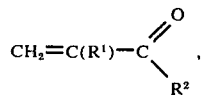

wherein $R^1$ is H or a methyl radical and $R^2$ is a $-OR^3$, or $-NR^3R^4$ radical, with $R^3$ and $R^4$ in such radical being H or a hydrophilic radical, particularly a hydroxyalkyl radical containing from 1 to 2 carbon atoms or a methoxy methyl radical. Non-limiting examples of such compounds are acrylic acid, methacrylic acid, acrylamide, methacrylamide, N-hydroxy-methylacrylamide, N-hydroxymethyl- methacrylamide, N-methoxymethylacrylamide, N-methoxymethyl- methacrylamide, ethyleneglycol monoacrylate, ethyleneglycol monomethacrylate and the like. The choice of the monomer depends mainly on economic conditions, and, for that reason, acrylic acid, methacrylic acid, acrylamide and mixtures thereof preferably are used. Reference to water-soluble monomer and water-soluble uncross-linked polymer also shall include mixtures of ethylenically unsaturated monomers containing a greater part of monomers whose uncross-linked polymers are water-soluble and a lesser part of monomers whose uncross-linked polymers are water-insoluble.

The amount of said water soluble monomer used depends on many factors such as alumina hydrogel and hydrosol amount, monomer type, desired apparent density for the final calcined beads, etc. Generally, the amount of said monomer is between 0.25 and 20% by weight of the aqueous mixture. It has been observed that the beads obtained in accordance with the process of the present invention depends on the respective amounts of alumina hydrogel and hydrosol and of monomer. Preferably, the amount of said monomer used is in an amount corresponding to about 5 to 150% of the alumina hydrogel and hydrosol weight. Higher amounts of monomers may induce a disaggregation of the beads when these latter are calcined. Too low an amount of monomers result in the production of beads which are not easily handled and not very firm. In order to obtain beads which present, after calcination, interesting properties with regard to density and mechanical strength, the aqueous mixtures preferably used contain an amount of monomer corresponding to about 5 to 75% by weight of alumina hydrogel plus hydrosol (based on oxide).

The starting mixture is dispersed into a substantially water-immiscible fluid, having a temperature between about 50° and 105° C at atmospheric pressure. Preferably, the aqueous mixture is introduced with the aid of calibrated orifices or nozzles in order to obtain a subdivision of said mixture in the form of droplets which are dispersed into the fluid. The residence time of the droplets in the fluid must be sufficient to permit the polymerization of the monomers. This water-immiscible fluid may be a gas, such as dry air, which is introduced into a tower in counter-current flow to the droplets of the starting aqueous mixture. Another advantageous embodiment of the invention is the using, as such fluid, a water-immiscible liquid. This liquid may have a density higher than that of the beads to be prepared. In such instance, the starting aqueous mixture is introduced as droplets at the bottom of a column containing the liquid and the beads formed are then recovered on the surface of the liquid. Another embodiment consists in using a liquid medium whose density is lower than that of the beads such as mineral oil. A generally used such technique is described in U.S. Pat. No. 2,620,314. Such technique consists in using a column filled with hot oil in which droplets of an aqueous mixture are let to fall, the residence time of the droplets in the oil being sufficient to allow the polymerization of the polymer. Temperature of the liquid is at least equal to about 50° C, in order to reduce the polymerization time. Temperatures higher than about 105°–110° C result in evaporation of water and a disaggregation of beads, unless the process is carried out under pressure. According to a preferred embodiment, the temperature of the water-immiscible liquid is between 75° and 100° C and the pressure at about atmospheric pressure.

In order to reduce the time needed for the beads to form, it is advantageous to use means for promoting the polymerization of the monomers. Free radical catalysis techniques with peroxidic compounds are quite useful and particularly useful are the redox system catalysis, which consists of using as catalyst a combination of a peroxidic compound and a reducing agent. Persulphuric acid, hydrogen peroxide, perboric acid and their salts, particularly sodium, potassium or ammonium persulphates and the water soluble peracids, such as peracetic acid, are examples of useful peroxidic compounds. Reducing agents may be selected from the group consisting of sodium thiosulphate, solium hyposulphite or dithionite, sodium or potassium bisulfite, N, N, N', N'-tetramethylethylene-daimine, sodium formaldehydro-sulfoxylate, hydrazine, ascorbic acid, etc. A part of the reducing agent may be introduced into the starting aqueous mixture, the other part being added into the water-immiscible fluid in which the polymerization is performed to the exent such reducing agent is soluble in the fluid. It may also be added into the vessel in which the beads are recovered.

The term "polymerization catalyst", as used herein, includes the peroxidic compound when this latter is used with or without reducing agent. The amount of polymerization catalyst can vary widely and it depends on the content of inhibitors present in the monomers used. Generally, the amount of polymerization catalyst is between about 0.05 and 1.5% by weight of aqueous mixture when the monomers are substantially free from inhibitors.

The mixture subjected to polymerization may contain a cross-linking agent which has functional groups so that the polymer chains are linked together and form a three dimensional structure. Cross-linking agents may be 1,3-di(acryl or methacryl-amidomethyl)-2-imidazolidone, hexahydrotriacryloyl- triazine, N,N'-methylidine-bis-acrylaminde, such as N,N'- methylene-bis-acrylamide and N,N'-ethylidene-bis-acrylamide when the acrylic monomer used has a amide group, an aldehydic compound may be used as cross-linking agent, such as formaldehyde and glyoxal. Glyoxal reacts with a part of acrylamide to form N, N'-dihydroxyethylene-bis-acrylamide. It is not necessary to add a cross-linking agent when the acrylic monomers are in an acid medium, but it may be useful to reduce attrition of the beads formed. The amount of corss-linking agent does not generally exceed 1% of the weight of the aqueous mixture although higher amounts may be used, but without any significant advantage.

The beads obtained are subjected to a thermal treatment. They are dried at a temperature of about 110° C and calcined by progressively increasing the temperature to about 400° to 800° C to 700° C. The organic matter which is contained in the beads is destroyed by this calcination treatment and finally beads consisting of firmly agglomerated alumina are obtained.

The process of the present invention is very flexible and permits preparation of a wide variety of catalysts, containing one or more active catalytic agents, by introducing into the starting aqueous mixture one or more of these agents or compound-generating catalytic agents. According to another embodiment of the process of the invention, one of these agents or one of these compounds is introduced into the starting aqueous mixture, thereafter the beads obtained are impregnated, still wet or dried, or dried and calcined, with another catalytic agent or another compound which generates another catalytic agent. By either method, after calcination, a catalyst in the form of beads is obtained, which consists of a solid agglomerate consisting of an alumina carrier and one or more catalytic agents. The catalysts obtained are particularly suitable for heterogeneous catalytic reactions wherein the catalyst must have a high mechanical and thermal strength.

The following examples are presented to illustrate the present invention but are not to be considered limiting. Except as otherwise specifically stated, the percentages indicated in the examples are expressed by weight. In the examples, the mechanical resistance of the beads is expressed by the crushing resistance measured with the Tablet Hardness Tester apparatus (of Manestry Machines, Ltd., Liverpool, Great Britain) in which the bead is placed between two plates, one of which is fixed and the other moves for increasing weight. The mechanical resistance values given in the examples are the average values of experiments performed on 5 beads.

EXAMPLE 1

Alumina hydrogel was prepared by treating aluminium sulphate with caustic soda up to pH = 9. The gel obtained was purified by several waterwashes, and thereafter dried at 110° C, crushed and sieved. Alumina hydrosol was prepared by digesting aluminium turnings into aqueous aluminium chloride. Thereafter water, the alumina hydrogel and the hydrosol were mixed together. The resulting mixture was heated at 95° C, with stirring for 1 hour. After cooling, the evaporated water was replaced, and the mixture was subjected to a vigorous stirring. To the mixture was then added, acrylic acid, di-hydroxyethylene-bis-acrylamide, ammonium persulphate and sodium bisulphite, The resulting aqueous mixture had the following composition:

| | |
|---|---|
| alumina hydrogel | 8% (based on $Al_2O_3$) |
| alumina hydrosol | 2% (based on $Al_2O_3$) |
| molybdenium oxide | 1.3% |
| acrylic acid | 1.5% |
| dihydroxyethylene-bis-acrylamide | 0.075% |
| ammonium persulphate | 0.2% |
| sodium bisulphite | 0.02% |
| water | remainder |

This mixture was introduced, dropwise, into the head of a column containing paraffinic oil heated at 95° C. Beads were recovered at the bottom of the column. The beads were dried and calcined. After calcination, the beads had a crushing strength of 4 kg.

These catalyst beads were used for the reforming of gasoline, at a temperature of 550° C, under a pressure of 3.5 kg/cm2 and with a space velocity of 1. The following results were obtained:

|  | Before reforming | After reforming |
|---|---|---|
| Boiling rante | 71 – 241° C | 48 – 211° C |
| Octane index (with 3 cc of lead tetraethyl) | 71 | 88 |

EXAMPLE 2

The procedure described in Example 1 was repeated, except that an aqueous mixture containing 1% of acrylic acid was used. The catalyst beads, obtained after calcination, had an apparent density of 0.7 g/ml and a crushing strength of 5.1 kg.

EXAMPLE 3

The procedure described in Example 1 was repeated except that an aqueous mixture containing 2% of acrylic acid was used. The catalyst beads, obtained after calcination, had an apparent density of 0.57 g/ml and a crushing strength of 4.6 kg.

EXAMPLE 4

The procedure describe in Example 1 was repeated except that the following mixture was injected dropwise into a column containing paraffinic oil heated at 95° C.

| alumina hydrogel | 8% (based on $Al_2O_3$) |
|---|---|
| alumina hydrosol | 2% (based on $Al_2O_3$) |
| chromium oxide | 1% |
| acrylic acid | 1% |
| acrylamide + glyoxal | 0.05% |
| ammonium persulphate | 0.21% |
| sodium bisulphite | 0.021% |

The mixture of acrylamide and glyoxal comprised these constituents in a molar ratio of acrylamide to glyoxal eqaul to 2 : 1. The beads were recovered at the bottom of the column containing oil. They were maintained in a 5.6% ammonia solution. After drying and calcining at 700° C, catalyst beads were obtained consisting of alumina containing 9.1% of $Cr_2O_3$. They had an apparent density of 0.55 g/ml and a crushing strength of 2.9 kg.

This catalyst was used for dehydrogenating butane at a temperature of 550° C. n-butene was obtained with a 31.1 mo 1% yield.

EXAMPLE 5

The procedure described in Example 1 was repeated to prepare an aqueous mixture containing:

| alumina hydrogel | 8% (based on $Al_2O_3$) |
|---|---|
| alumina hydrosol | 2% (based on $Al_2O_3$) |
| cobalt nitrate | 0.3% (based on CoO) |
| Acrylamide | 3% |
| Ammonium persulphate | 0.3% |
| sodium formaldehyde-sulphoxylate | 0.03% |

This mixture was injected dropwise at the bottom of a column containing Phenoclor DP4 (chlorinated diphenyl sold by PROGIL S.A. and having a density of 1.39 at 100° C) heated at 95° C. The beads were recovered on the surface of the liquid. They were maintained in a 5.6% ammonium solution for 12 hours. Thereafter, they were dried at 110° C and calcined at 700° C. The catalyst beads consisted of $Al_2O_3$ containing 2.9% of CoO and had an apparent density of 0.65 g/ml and a crushing strength of 1.7 kg.

This catalyst was found to be useful for hydrogenating pyridine into piperidine at 150° C and 200° atmospheres.

EXAMPLE 6

The procedure described in Example 1 was repeated with an aqueous mixture containing:

| alumina hydrogel | 6% (based on $Al_2O_3$) |
|---|---|
| alumina hydrosol | 4% (based on $Al_2O_3$) |
| zinc oxide | 0.4% |
| chromium oxide | 0.4% |
| acrylic acid | 1.5% |
| dihydroxyethylene-bis-acrylamide | 0.075% |
| ammonium persulphate | 0.083% |
| sodium bisulphite | 0.0083% |

The calcined beads consisted of $Al_2O_3$ containing zinc oxide and chromium oxide in a weight ratio of 1 : 1. They had an apparent density of 0.61 g/ml and a crushing strength of 3.4 kg.

This catalyst was found to be useful for methanol synthesis from CO and $H_2$.

EXAMPLE 7

The procedure described in Example 6 was repeated but with a starting aqueous mixture containing 1.25% of acrylic acid and 0.25% of acrylonitrile instead of 1.50% of acrylic acid. The catalyst beads obtained had the same characteristics as those of the beads obtained in Example 6.

EXAMPLE 8

3.18 g of alumina hydrogel containing 24% of water, 2.85 g of alumina hydrosol containing 11.4% of aluminium and 19 g of water were mixed together. This mixture was heated at 95° C during 1 hour. After cooling, an amount of water equal to the amount of evaporated water was added. Thereafter, while stirring, 2.54 g of a solution containing 35.5% of acrylamide and formaldehyde in a molar ration of ½ based on acrylamid, 21 g of an aqueous sodium silicate solution containing 27% of $SiO_2$, 0.5 g of finely divided magnesium oxide, 3 ml. of a 10% ammonium persulphate solution and 1.5 ml of a 2% sodium bisulphite solution was added. This mixture was injected dropwise into a column containing paraffinic oil heated at 99° C. The beads formed were water-washed, dried at 120° C and calcined at 500° C. The calcined beads consisted of $Al_2O_3$ containing 13.5% of $SiO_2$ and 14.2% of MgO.

This catalyst was found to be useful for isomerizing 2,2--dimethyl-butane into 2,3-dimethyl-butane.

EXAMPLE 9

An aqueous mixture was prepared containing the following:

| alumina hydrogel | 6.4% (based on $Al_2O_3$) |
|---|---|
| alumina hydrosol | 4.3% (based on $Al_2O_3$) |
| nickel oxide | 0.32% |
| methacrylic acid | 3.2% |
| ethyleneglycol monomethacrylate | 0.6% |
| dihydroxyethylene-bis-acrylamide | 0.18% |
| ammonium persulphate | 0.7% |

| | |
|---|---|
| sodium bisulphite | 0.07% |

This mixture was subjected to a low pressure in order to inject it dropwise into a column containing paraffinic oil heated at 102° C. The beads which formed were recovered and waterwashed, aged in a 5.6% ammonia solution for 12 hours. Thereafter they were dried and calcined. The calcined beads consisted of Al$_2$O$_3$, containing 2.9% of nickel oxide, and had the following properties: apparent density - 0.52 g/ml; crushing strength - 1.2 kg. A part of these beads were subjected to a hydrogenation treatment at 470° C. A nickel on alumina support catalyst was obtained. This catalyst was found useful for hydrogenating benzene into cyclohexane.

Another part of the beads formed above were impregnated with ammonium heptamolybdate. After drying and calcining, the beads obtained contained 2.5% of nickel oxide and 15% of molbdenium oxide. This catalyst was found to be useful for hydrodesulphurizing gasoil.

EXAMPLE 10

An aqueous mixture was prepared containing the following:

| | |
|---|---|
| alumina hydrogel | 16.8% (based on Al$_2$O$_3$) |
| alumina hydrosol | 3.2% (based on Al$_2$O$_3$) |
| chloroplatinic acid | 0.16% |
| N-hydroxymethylacrylamide | 3.8% |
| dihydroxyethylene-bis-acrylamide | 0.185% |
| ammonium persulphate | 0.15% |
| sodium bisulphite | 0.015% |

The beads obtained otherwise according to the procedure described in Example 1, were dried and calcined at 500° C. The catalyst beads obtained consisted of Al$_2$O$_3$ containing 0.5% of platinium.

These beads were used for reforming naphtha at a temperature of 550° C and under a pressure of 3.5 kg/cm2. The following results were obtained.

| | Before reforming | After reforming |
|---|---|---|
| Boiling (° C) | 130 – 195° C | 82 – 215° C |
| Octane index (with 3 cc of lead tetraethyl) | 71 | 93 |

EXAMPLE 11

The procedure described in Example 10 was repeated but chloroplatinic acid was substituted by 0.4% of RhCl$_3$ x H$_2$O (38.55% of Rh). The beads obtained consisted of Al$_2$O$_3$ containing 0.75% or rhodium. This catalyst was found useful for dehyroisomerizing methylcyclopentane into benzene.

What is claimed is:

1. A process for preparing catalysts in the form of beads comprising at least a catalytic agent and an alumina carrier, said process comprising dispersing as droplets in a hot and substantially water-immiscible fluid, an aqueous mixture which comprises finely divided alumina hydrogel, alumina hydrosol, the alumina hydrogel and hydrosol being in a weight ratio of alumina hydrogel to alumina hydrosol (based on Al$_2$O$_3$) of between 99:1 and 50:50, and 0.05 to 35% by weight of a compound capable of generating a catalytic agent by thermal or chemical treatment and 0.25 to 20% by weight of a water soluble monomer whose uncrosslinked polymer is water soluble or forms a gel, said monomer comprising an acrylic compound of the general formula:

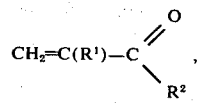

wherein, R$^1$ is selected from the group consisting of H and a methyl radical, R$^2$ is selected from the group consisting of the —OR$^3$, and –MR$^3$R$^4$ radicals wherein R$^3$ and R$^4$ are selected from the group consisting of H and a hydrophilic radical, such aqueous mixture including said monomer, being dispersed as droplets into the hot fluid, carrying out polymerization of said droplets in said hot fluid employing thermal polymerization techniques or free radical catalytic polymerization techniques until said polymerization is substantially complete, recovering beads from said water immiscible fluid and drying and calcining said beads.

2. A process for producing catalytic beads comprised of a catalytic agent and alumina, said process comprising: (a) producing an aqueous mixture comprising finely divided alumina hydrogel and hydrosol in a weight ratio of alumina hydrogel to alumina hydrosol (based on Al$_2$O$_3$) of between 99.1 and 50:50, 0.05 to 35% by weight of a compound which is capable of generating a catalytic agent by thermal or chemical treatment and 0.25 to 20% by weight of a monomer whose uncross-linked polymer is water soluble or forms a gel, said monomer comprising an acrylic compound of the general formula:

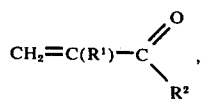

wherein R$^1$is selected from the group consisting of H and a methyl radical, R$^2$ is selected from the group consisting of the —OR$^3$, and –NR$^3$R$^4$ radicals wherein R$^3$ and R$^4$ are selected from the group consisting of H and a hydrophilic radical, (b) dispersing said aqueous mixture as droplets into a practically water-immiscible hot fluid, (c) substantially polymerizing said polymer contained in each droplet of said aqueous mixture employing thermal polymerization or free radical catalytic polymerization under polymerization conditions, (d) recovering beads from said water-immiscible fluid, said beads consisting of alumina hydrogel and hydrosol and of said compound capable of generating an active catalytic agent, agglomerated by the polymer, (e) drying said beads, and (f) calcining said beads in order to obtain beads consisting of alumina and said catalytic agent.

3. A process for producing catalytic beads comprised of a catalytic agent and alumina, said process comprising preparing an aqueous mixture containing from 5 to 29.95% bu weight, (based on aluminium oxide) of finely divided alumina hydrogel and hydrosol, the weight ratio of alumina hydrogel to hydrosol (based on Al$_2$O$_3$) being between 99:1 and 50:50, 0.05 to 10% by weight of a compound capable of generating an active catalytic agent by thermal or chemical treatment (based on catalytic constituent), the total amount of hydrogel, hydrosol and generating agent not exceeding 30% of said aqueous mixture weight, 0.25 to 20% by weight of a water soluble monomer, ethylenically unsaturated, whose uncross-linked polymer is water soluble or forms a gel, said monomer being an acrylic compound of the general formula:

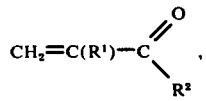

wherein R$^1$ is selected from the group consisting of H and a methyl radical, R$^2$ is selected from the group consisting of the –OR$^3$, and —NR$^3$R$^4$ radicals wherein R$^3$ and R$^4$ are selected from the group consisting of H and a hydrophilic radical, and 0.05 to 2% of a free radical polymerization catalyst, dispersing said aqueous mixture as droplets into a water immiscible fluid having a temperature of 50° to 105° C at atmospheric pressure, maintaining said droplets in said fluid until beads are formed and said beads become hard, and thereafter drying and calcining said beads.

4. The process of claim 1 wherein said aqueous mixture contains 7.5 to 20% by weight of an alumina hydrogel and hydrosol mixture.

5. The process of claim 1 wherein said weight ratio is between 18:15 and 55:45.

6. The process of claim 1 wherein said monomer is used in an amount corresponding to about 5 to 150% of the weight of the alumina hydrogel-alumina hydrosol mixture.

7. The process of claim 1 wherein the polymerization of said aqueous mixture is carried out by dispersing said aqueous mixture in the form of droplets, and passing these droplets in counter-counter flow to a dry hot gas.

8. The process of claim 1 wherein said polymerization of said aqueous mixture is carried out by dispersing said aqueous mixture in the form of droplets at the bottom of a column containing a liquid having a density higher than that of the beads, and recovering said beads on the surface of the liquid.

9. The process of claim 1 wherein the polymerization of the aqueous mixture is carried out by dispersing said aqueous mixture in the form of droplets at the head of a column containing a liquid having a density lower than that of the beads, and recovering said beads at the bottom of the column.

* * * * *